US008027524B2

(12) United States Patent
Ogura et al.

(10) Patent No.: US 8,027,524 B2
(45) Date of Patent: Sep. 27, 2011

(54) IMAGE DIAGNOSIS SUPPORT APPARATUS AND IMAGE DIAGNOSIS SUPPORT PROGRAM

(75) Inventors: Toshihiro Ogura, Tokyo (JP); Yoshihiro Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1104 days.

(21) Appl. No.: 11/795,486

(22) PCT Filed: Jan. 18, 2006

(86) PCT No.: PCT/JP2006/000644
§ 371 (c)(1),
(2), (4) Date: Jul. 18, 2007

(87) PCT Pub. No.: WO2006/077885
PCT Pub. Date: Jul. 27, 2006

(65) Prior Publication Data
US 2008/0118123 A1   May 22, 2008

(30) Foreign Application Priority Data

Jan. 19, 2005   (JP) ................................ 2005-011288

(51) Int. Cl.
*G06K 9/00* (2006.01)
(52) U.S. Cl. .............................. 382/128; 128/922; 378/4
(58) Field of Classification Search .................. 382/100, 382/128, 129, 130, 131, 132; 128/922; 378/4–27
See application file for complete search history.

(56) References Cited

U.S. PATENT DOCUMENTS

| 5,068,788 | A  | * | 11/1991 | Goodenough et al. | 382/131 |
| 6,990,222 | B2 | * | 1/2006  | Arnold            | 382/131 |
| 7,379,572 | B2 | * | 5/2008  | Yoshida et al.    | 382/128 |
| 7,466,848 | B2 | * | 12/2008 | Metaxas et al.    | 382/128 |
| 2003/0169915 | A1 | * | 9/2003 | Takeo            | 382/132 |

OTHER PUBLICATIONS

Abate, Nicola et al., "Estimation of adipose tissue mass by magnetic resonance imaging: Validation against dissection in human cadavers", Journal of Lipid Research, 1994, pp. 1490-1496, vol. 35.
Ogura, Toshihiro et al., "Evaluation of Intra-abdominal Fat Distribution Using X-ray CT data for Detection of Rectal Cancer", Japanese Society of Radiological Technology, Jun. 20, 2005, pp. 840-846, vol. 61, No. 6, Japan.
English Translation of International Preliminary Report on Patentability in PCT/JP2006/300644.

\* cited by examiner

*Primary Examiner* — Anand Bhatnagar
(74) *Attorney, Agent, or Firm* — Cooper & Dunham LLP

(57) ABSTRACT

An image diagnosis support apparatus according to the invention comprises an adipose distribution data computing device which figures out adipose distribution data measured of a desired site in a subject from at least one medical image; an abnormal shadow candidate detecting device which detects an abnormal shadow candidate based on the figured-out adipose distribution data; and a display device which displays the abnormal shadow candidate detected by the abnormal shadow candidate detecting device and the medical image in a manner of being related to each other.

20 Claims, 15 Drawing Sheets

FIG. 5
(A)
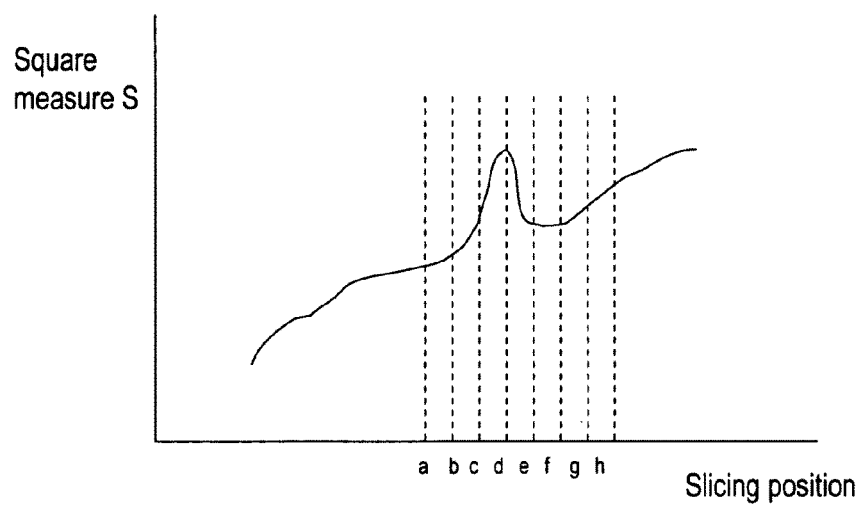
(B)
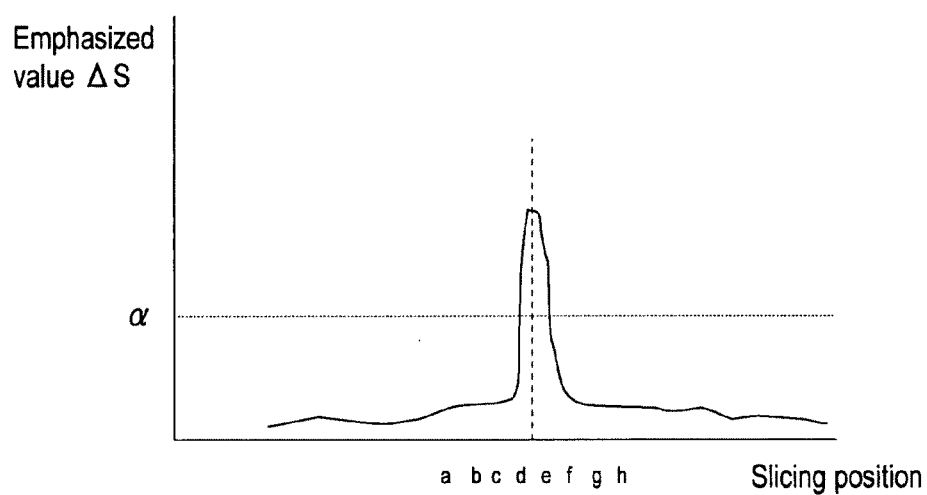

IMAGE DIAGNOSIS SUPPORT APPARATUS AND IMAGE DIAGNOSIS SUPPORT PROGRAM

TECHNICAL FIELD

The present invention relates to an image diagnosis support apparatus and an image diagnosis support program, and more particularly to a technique of presenting the suspected presence of abnormal shadow candidates based on medical images. The present application claims priority under the Paris Convention based on Japanese Patent Application No. 2005-011288 under the Patent Law of Japan, and is an application entitled to enjoy the benefits of Patent Application No. 2005-011288 by reference.

BACKGROUND ART

In order to strictly determine fatness, it is desirable to know the quantity of adipose and the intra-bodily distribution of adipose. In diagnosing obesity, assessment of the distribution of adipose is an important requirement.

Many studies have been made regarding the assessment of adipose on a two-dimensional plane by using an X-ray CT apparatus, an MRI apparatus or an ultrasonic apparatus. Non-Patent Document 1 reveals the close relevance of the accumulation of abdominal adipose to diabetes, abnormality in adipose metabolism factors involving risks of arteriosclerosis such as high blood pressure.

Non-Patent Document 1: Nicola Abate, Dennis Burns, Ronald M. Peshock, et al. (1994): Estimation of adipose tissue mass by magnetic resonance imaging: validation against dissection in human cadavers, Journal of Lipid Research 35, Radiological Society of North America: 1490-1496

However, Non-Patent document 1 makes no mention of the correlation between the intra-bodily accumulation of adipose, especially their abdominal accumulation, due to obesity and the probability of the presence, or the probability of incidence, of malignant tumors including cancer.

BRIEF SUMMARY

In an aspect of this disclosure, there is provided a technique of detecting any abnormal shadow candidate suspected to be a malignant tumor or the like based on relevance of the accumulation of adipose to the probability of the presence, or the probability of incidence, of a malignant tumor.

The inventor of the present application has found that it is possible to presume the presence of cancer or predict the physical susceptibility of a person to cancer by checking whether or not the person's adipose distribution curve manifests a shape which is absent in a normal (healthy) subject's distribution curve or whether not the subject's adipose distribution curve is highly correlated to an adipose distribution curve attributable to any disease he or she suffered in the past. In an aspect of this disclosure, there is provided an approach to detect any abnormal shadow candidate based on this finding.

In another aspect of this disclosure, an image diagnosis support apparatus that comprises an adipose distribution data computing device which figures out adipose distribution data measured of a desired site in a subject from at least one medical image; an abnormal shadow candidate detecting device which detects an abnormal shadow candidate based on the figured-out adipose distribution data; and a display device which displays the abnormal shadow candidate detected by the abnormal shadow candidate detecting device and the medical image in a manner of being related to each other.

In an aspect of this disclosure, there is provided an image diagnosis support program that causes a computer to execute a step of figuring out adipose distribution data measured of a desired site in a subject from at least one medical image; a step of detecting an abnormal shadow candidate based on the figured-out adipose distribution data; and a step of displaying the detected abnormal shadow candidate and the medical image in a manner of being related to each other.

Accordingly, it is possible to detect any abnormal shadow candidate suspected to he a malignant tumor or the like based on relevance of the accumulation of adipose to the probability of the presence, or the probability of incidence, of a malignant tumor.

BRIEF DESCRIPTION OF THE DRAWINGS

FIG. 5(A) shows the adipose area at each of points "a" through "h" on an adipose distribution curve and FIG. 5(B), an emphasized value figured out by filtering;

DESCRIPTION OF SYMBOLS

1 . . . Image diagnosis support system, 1a . . . LAN, 1b . . . X-ray CT apparatus, 10 . . . CPU, 11 . . . main memory, 12 ... magnetic disk, 13 ... display memory, 14 ... CRT, 15 ... mouse, 16 ... controller, 17 ... keyboard, 18 ... loudspeaker, 19 ... common bus, 20 ... image diagnosis support apparatus

BEST MODE FOR CARRYING OUT THE INVENTION

The image diagnosis support apparatus in a preferable mode for implementing the present invention will be described in detail with reference to accompanying drawings. The image diagnosis support apparatus in this mode for implementation is a medical image diagnostic apparatus, such as an X-ray CT apparatus for instance, which detects the presence or absence of any abnormal shadow candidate based on a plurality of tomograms (such as CT images, MRI images, ultrasonic (US) images or the like) collected regarding the object region of a subject or displays what are highly likely ones out of the medical image in which detected abnormal shadow candidates are shot. It can also display images on the way of such processing.

<First Mode for Implementation>

A first mode for implementation is an image diagnosis support system 1 which detects the presence or absence of and positional information on any abnormal shadow candidate by detecting a local maximum point (subpeak) based on adipose distribution data of a subject. This image diagnosis support system 1 analyzes total abdominal CT scan data and applies the distribution of abdominal adipose thereby examined to diagnosis support techniques.

In this mode for implementation, a plurality of medical images (CT images) from the upper edge of the liver to the anal region at 1 cm intervals upward and downward from the navel are acquired, an adipose region in the abdomen is measured from each medical image and, in this particular instance, the distribution of the areas of adipose regions is figured out. The image taking positions and slice thickness for a given subject are determined by the physician who shoots those images. If there is any local maximum point in this distribution of adipose areas, the presence of an abnormal shadow candidate is detected.

Although the area is the most suitable factor for this distribution assessment since the tomograms of the subject are two-dimensional images, any of, or the combination of, the number of pixels which is zero-dimensional information, the length which is one-dimensional information and the cubic measure which is three-dimensional information can be used, because the purpose is to know any indicator of the magnitude of adipose regions.

Figure 1:
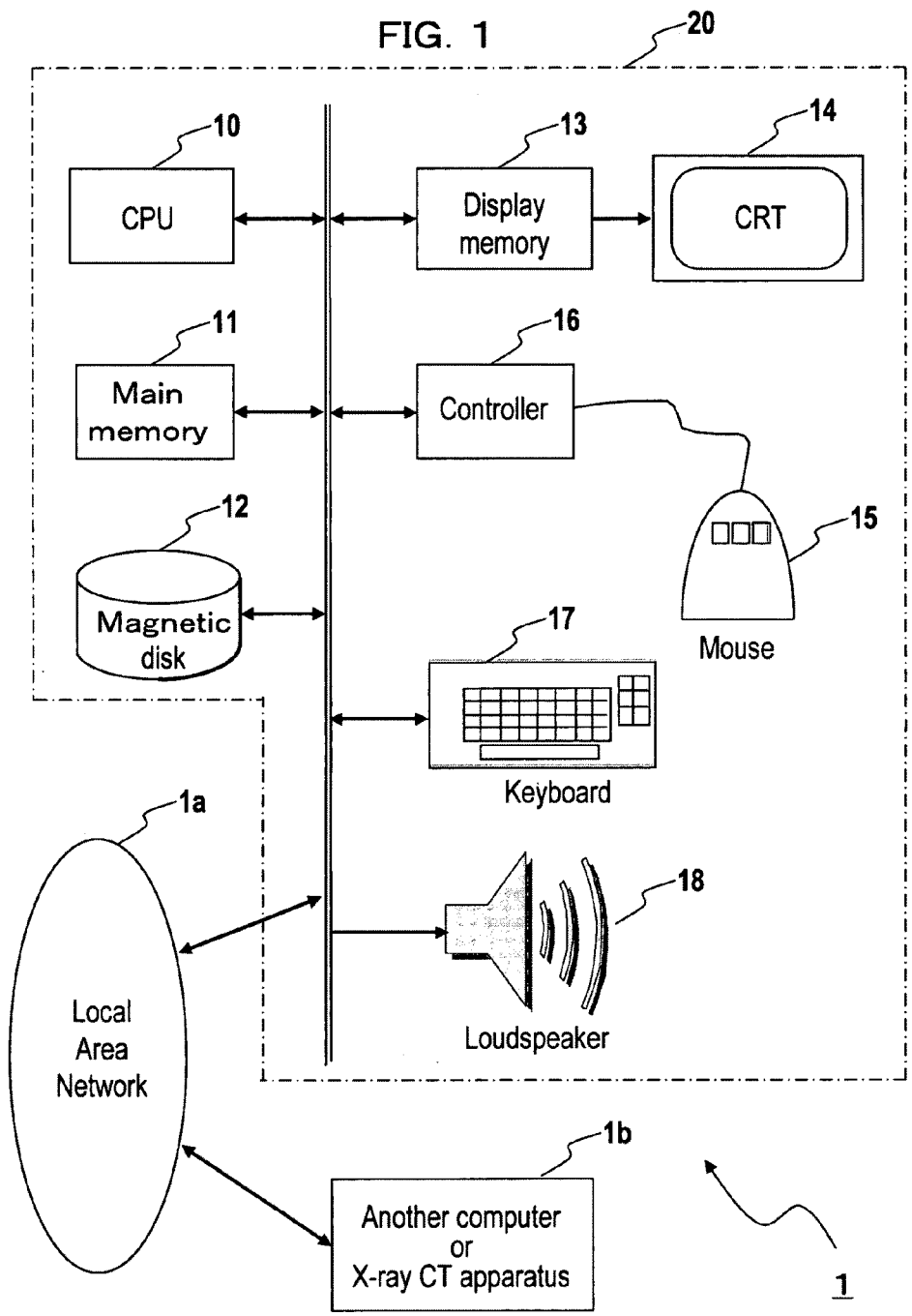
FIG. 1 is a block diagram showing the schematic configuration of an image diagnosis support system 1 to which the invention is applied.

FIG. 1 is a block diagram showing the schematic configuration of the image diagnosis support system 1 to which the invention is applied.

The image diagnosis support system 1 comprises a medical imaging apparatus 1b for acquiring a plurality of medical images regarding the object site of a subject and an image diagnosis support apparatus 20 for subjecting the medical images acquired by the medical imaging apparatus 1b to image processing. The medical imaging apparatus 1b and the image diagnosis support apparatus 20 are connected to each other via a LAN 1a.

The medical imaging apparatus 1b is an X-ray CT apparatus, an MRI apparatus or the like. Incidentally, the medical imaging apparatus 1b may be any device that can collect medical images, such as a medical image management system which stores and manages medical images (Pictures Archive and Communication System: PACS) or some other computer. In the following paragraphs, an X-ray CT apparatus 1b will be described as an example of medical imaging apparatus 1b. The example of medical images will be CT images (tomograms) in the description.

The image diagnosis support apparatus 20 comprises a central processing unit (CPU) 10 which controls the operations of various constituent elements, a main memory 11 in which a control program for the device is stored, a magnetic disk 12 in which a plurality of sets of medical image data, programs and the like are stored, a display memory 13 for temporarily storing image data to be displayed, a CRT 14 as a display unit for displaying images based on image data from this display memory 13, a mouse 15 for manipulating software switches on the screen and the controller 16 thereof, a keyboard 17 provided with keys and switches for setting various parameters, a loudspeaker 18 and a common bus 19 for connecting these constituent elements.

Although the image diagnosis support apparatus 20 in this mode for implementation as described here has only the magnetic disk 12 as a memory device other than the main memory 11, it may as well be provided, in addition to it, a floppy disk drive, hard disk drive, CD-ROM drive, magneto-optic disk (MO) drive, ZIP drive, PD drive or DVD drive. Furthermore, the image diagnosis support system 1 may be provided with a memory device on one or another of various communication networks such as the LAN 1a, the Internet and telephone lines via a communication interface not shown.

Next, the configuration of a program installed in the image diagnosis support apparatus 20 will be described. The CPU 10 reads the program to be described below out of the magnetic disk 12, and loads it into the main memory 11 for execution.

The program causes a computer to execute various steps including an adipose distribution data computing step of computing an adipose distribution data measured of a desired site of the subject from at least one medical image, an abnormal shadow candidate detecting step of detecting an abnormal shadow candidate based on the computed adipose distribution data, a display step of displaying the abnormal shadow candidate detected at the abnormal shadow candidate detecting step and the medical image in a manner of being related to each other, an abnormal shadow candidate extracting step of extracting the abnormal shadow candidate detected at the abnormal shadow candidate detecting step from the medical image.

In this mode for implementation, an adipose distribution curve of which one axis represents the position in the subject and the other represents the distribution of the adipose area acquired from the medical image shot in that position is generated at the adipose distribution data computing step. At the display step, the generated adipose distribution curve is displayed.

At the abnormal shadow candidate detecting step, at least one local maximum point in the adipose distribution curve is detected, and an abnormal shadow candidate is detected based on the detected local maximum point. At the abnormal shadow candidate extracting step, the abnormal shadow candidate is extracted from a medical image by computer aided detection (CAD). At the display step, the abnormal shadow candidate extracted at the abnormal shadow candidate extracting step and the medical image are displayed in a manner of being related to each other.

Figure 2:
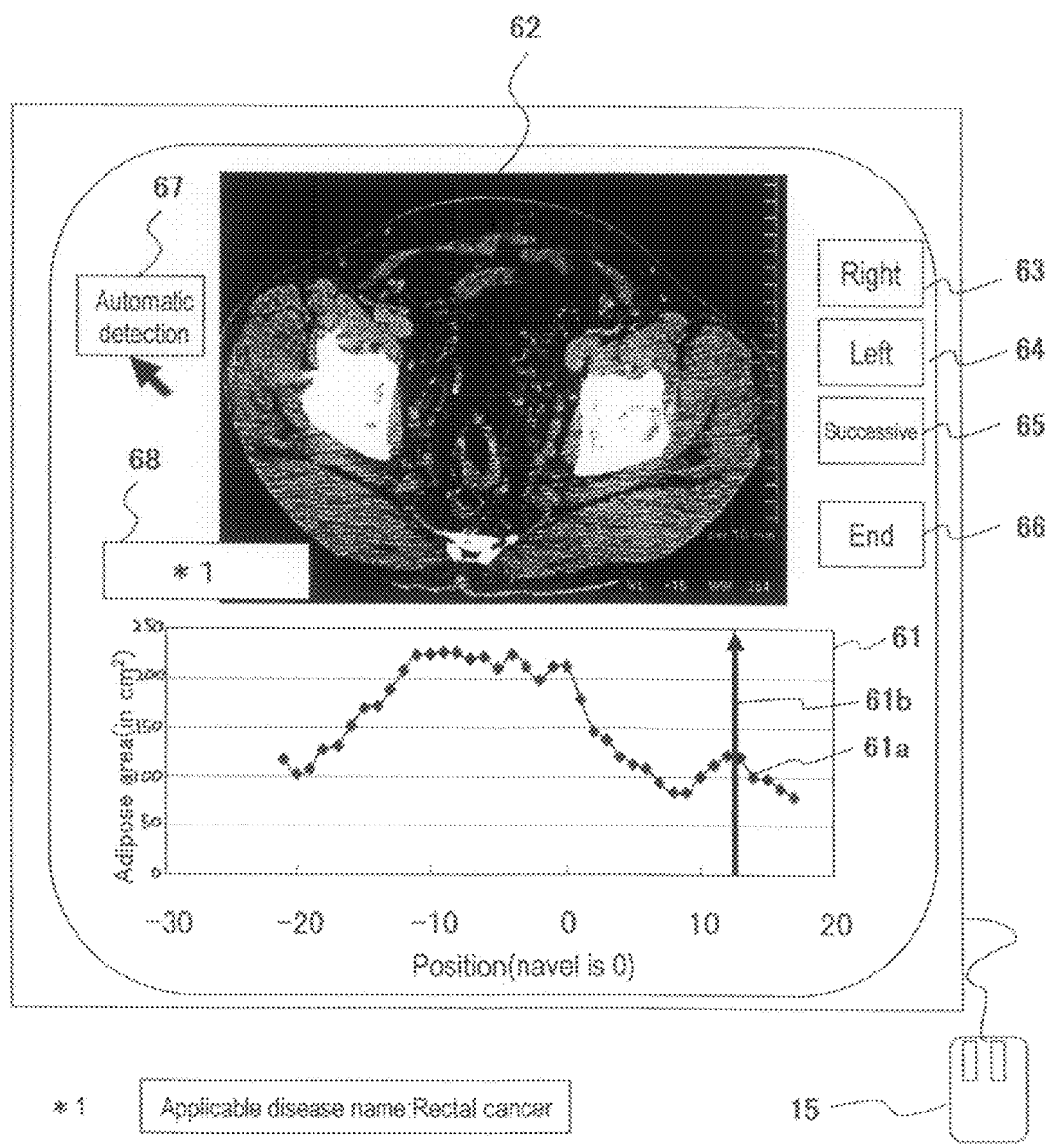
FIG. 2 shows a state in which the adipose distribution curve and a medical image of a subject.

FIG. 2 shows an example of screen display in the first mode for implementation. In the example of FIG. 2, an adipose distribution graph 61, a medical image 62, a right button 63, a left button 64, a successive button 65, an end button 66, an automatic detection button 67 and a message display area 68 are displayed.

The axis of abscissas in the adipose distribution graph 61 represents the position (in cm) of the subject in the direction of the bodily axis and the axis of ordinates of the same, an adipose area (in $cm^2$). On the axis of abscissas, the 0 position corresponds to the position of the navel, while the minus direction (to the left of 0 on the axis of abscissas) represents the direction toward the upper part of the abdomen (liver) and the plus direction (to the right of 0 on the axis of abscissas 0), the direction toward the lower part of the abdomen (anus).

An adipose distribution curve 61a and a pointer 61b which designates positions on the adipose distribution curve 61a drawn on the adipose distribution graph 61. The adipose distribution curve 61a is a curve resulting from the plotting of adipose area information acquired from medical images shot in different positions on the adipose distribution graph 61. The pointer 61b is intended for designating any desired position on the adipose distribution curve 61a; the medical image 62 corresponding to the position designated by the pointer 61b on the adipose distribution curve 61a is displayed on the CRT 14.

The operator designates a desired position on the adipose distribution curve 61a by moving the pointer 61b right or left with the mouse 15. At the abnormal shadow candidate detecting step, the medical image 62 in the designated position corresponding to the pointer 61b on the adipose distribution curve 61a is read out of the magnetic disk 12, and the read-out medical image 62 is displayed on the CRT 14. Although a method of designating a position on the adipose distribution curve 61a the pointer 61b is described here, it is also possible to use a configuration in which an input column in which positions relative to the navel as the reference position 0 is displayed in a table form instead of this pointer 61b and the operator designates a position on the adipose distribution curve 61a by inputting the desired value to that displayed table thereby to cause the medical image corresponding to that position to be displayed. By using such a configuration, the appropriate position to be designated on the adipose distribution curve can be duly designated without having to be conscious of the reference position. Although the example described above uses the position of the navel as the reference position 0, the choice is not limited to this example.

When the operator clicks the right button 63 on the screen with the mouse 15, the pointer 61b moves rightward, and a medical image 62 in a position closer than the displayed medical image 62 toward the lower part of the abdomen is displayed. Similarly, when the operator clicks the left button 64 on the screen with the mouse 15, the pointer 61b moves leftward, and a medical image 62 in a position closer than the medical image 62 toward the upper part of the abdomen is displayed. Further, when the operator clicks the successive button 65 on the screen with the mouse 15, medical images 62 are displayed, switched over successively from one to next toward the lower part or the upper part of the abdomen. In the successive switched-over displaying, the position of the pointer 61b is altered, interlocked with the switching-over of the medical image 62. The successive switched-over displaying is ended when the operator clicks the end button 66 during the execution of the successive switched-over displaying.

The right button 63 and the left button 64 may be so configured as to move on the adipose distribution curve 61a in a prescribed range at a time, for instance 1 cm by 1 cm or, where the adipose distribution curve 61a has a plurality of local maximum points, may as well function as buttons to move the pointer 61b to another local maximum point to the left or the right or the vicinity of that local maximum point. The successive button 65 may also function as a button to successively display medical images 62 corresponding to the positions of local maximum points on the adipose distribution curve 61a.

When the automatic detection button 67 is clicked with the mouse 15, any abnormal shadow candidate suspected to represent cancer is extracted from the medical image 62 at the abnormal shadow candidate extracting step. The extracted abnormal shadow candidate may be indicated at the display step in a different way displaying from non-abnormal shadow candidates in the medical image 62, for instance by using a different display color, superposing a marker, flashing the abnormal shadow candidate area or combining some of these display modes.

On the message display area 68, the adipose area measured at the adipose distribution data computing step, the name of the disease the subject has presumably contracted according to the medical image 62 and other items are displayed. In FIG. 2, "rectal cancer" is displayed as the name of the suspected disease.

The adipose distribution curve 61a in FIG. 2 has a local maximum point of abdominal adipose emerging in the neighborhood of 13 [cm] from the navel (0 on the axis of abscissas) toward the lower part of the abdomen. In a medical image of a position characterized by variations in data such as a local maximum point (characteristic point), an abnormal shadow candidate (suspected cancer) is often present. Then, the parallel displaying of the medical image 62 and the adipose distribution graph 61 corresponding to the characteristic point makes possible reading of the medical image 62 in which the abnormal shadow candidate is present.

Further by displaying only the medical image 62 corresponding to the characteristic point which suggests the onset of a disease is displayed, with others skipped in the parallel displaying of medical images 62 corresponding to characteristic points and the adipose distribution graph 61, a medical image 62 that is more likely to indicate the presence of an abnormal shadow candidate can be displayed with priority. The characteristic points in this context include, besides local maximum points, any other varying points of data such as minimum points and points of inflection.

Figure 3:
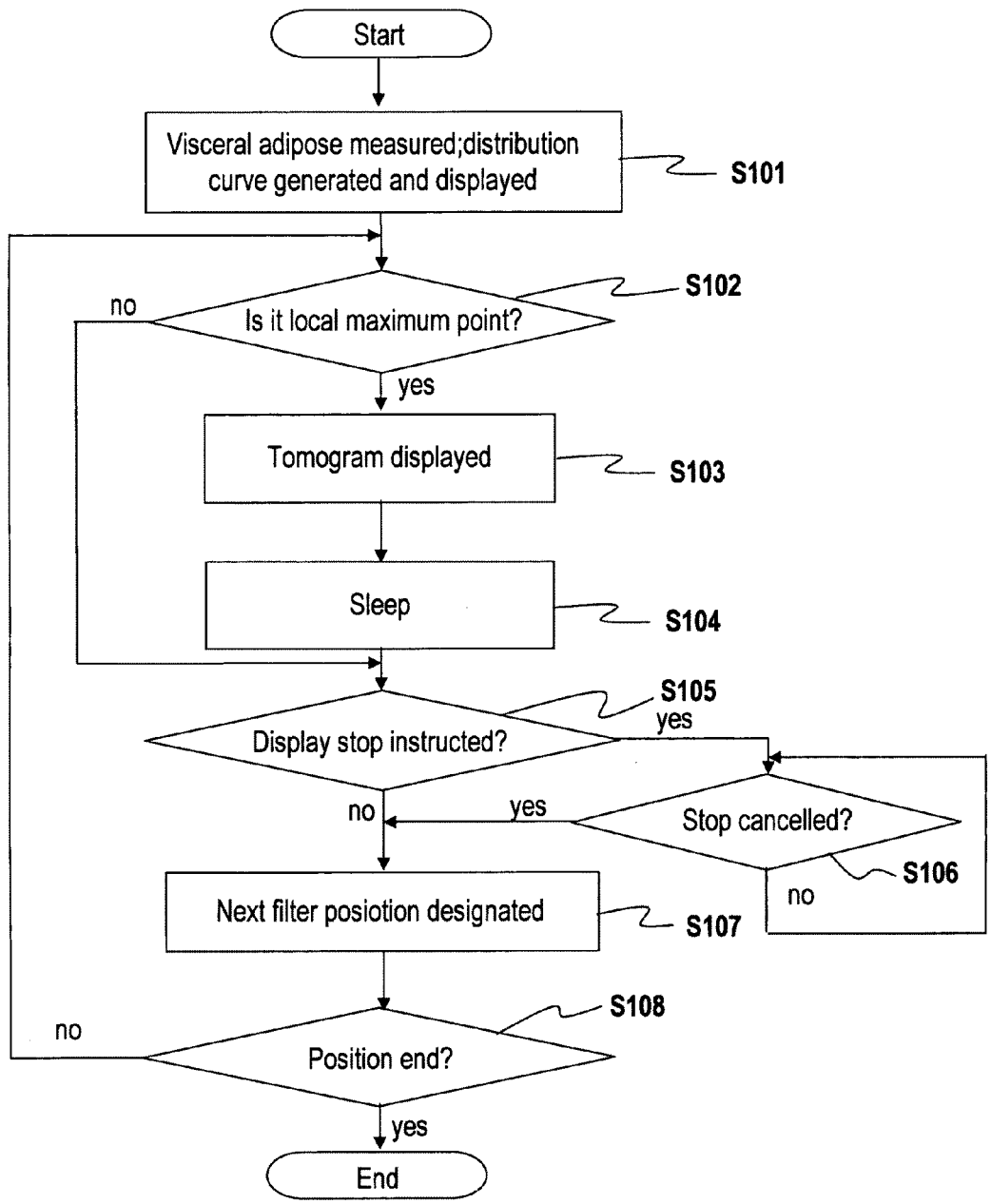
FIG. 3 is a flow chart of processing to draw an adipose distribution curve based on a medical image and detecting the local maximum point of the adipose distribution curve.

Next, processing in this mode for implementing the invention will be described with reference to FIG. 3. FIG. 3 is a flow chart of processing by the image diagnosis support apparatus 20 to draw an adipose distribution curve of the subject and to detect the local maximum point of the adipose distribution curve.

(Step S101)

At the adipose distribution data computing step, the adipose area is measured of each of a plurality of medical images acquired from the subject in successively varied spatial positions. In this mode for implementation, the abdominal adipose area is measured of medical images acquired in a prescribed range around the navel (from the liver to the anus) of the subject.

The abdominal adipose area in this context means the remaining area of the total adipose area after subtraction of the subcutaneous adipose area. The abdominal adipose will be hereinafter referred to as simply "adipose area".

Before measuring the abdominal adipose area, the abdominal adipose area may be extracted by manual tracing with the mouse as processing to extract the abdominal adipose area, or the abdominal adipose area may be automatically extracted from the medical image by threshold processing using CT values corresponding to adipose tissues. At the adipose distribution data computing step, the extracted abdominal adipose area is measured, and the adipose area information obtained by the measurement, positions in the direction of the bodily axis of the subject and the medical images picked up in the respective positions are matched with one another and stored onto the magnetic disk 12.

At the adipose distribution data computing step, adipose distribution data according to which the position in the subject in which each medical image was picked up and adipose area information acquired from the medical image are matched with each other are generated. In this mode for implementation, the adipose distribution curve is generated as such adipose distribution data at the adipose distribution data computing step.

At the display step, the generated adipose distribution curve is displayed on the CRT 14. The adipose distribution curve 61$a$ in FIG. 2 is the adipose distribution curve generated at this step.

Figure 4:
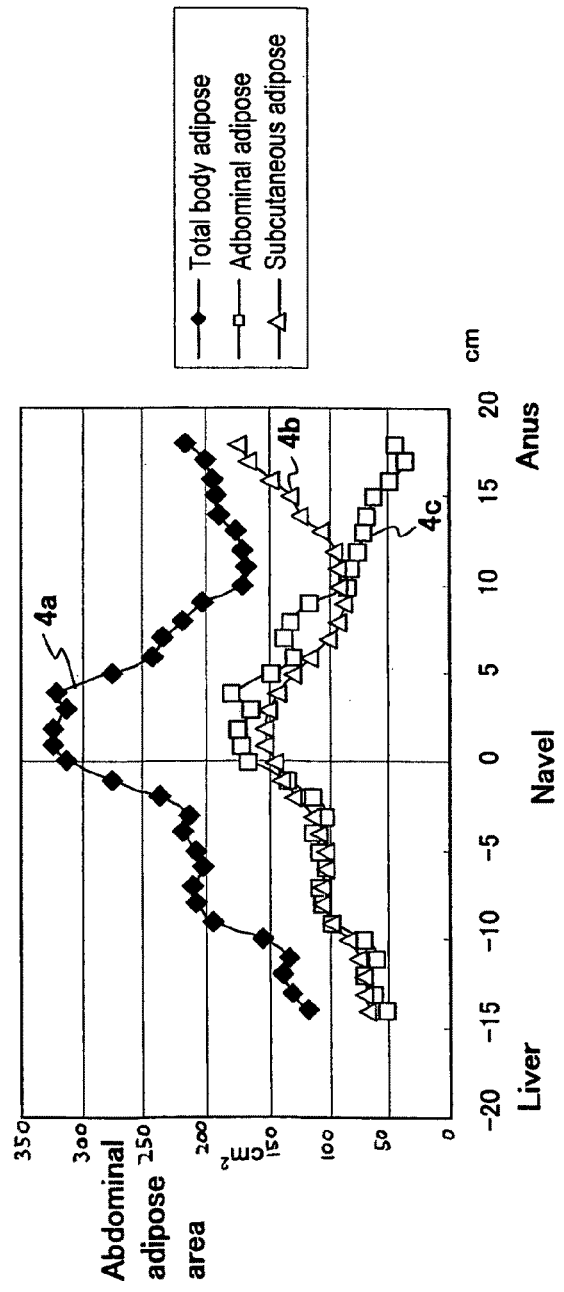
FIG. 4 shows an exemplary set of the adipose distribution curves of abdominal visceral adipose areas, subcutaneous adipose areas and total body adipose areas.

FIG. 4 is a schematic diagram illustrating adipose distribution curves, wherein distributions of total body adipose areas, subcutaneous adipose areas and abdominal adipose areas in a subject who has contracted all-around descending colon cancer relative to the position (the bodily axis) in the subject are shown. In FIG. 4, the axis of ordinates represents the square measure (in cm$^2$) and the axis of abscissas, the position in the subject (in cm). The 0 position on the axis of abscissas 0 represents the position of the navel, the minus direction (to the left of the axis of abscissas 0) represents the direction toward the upper part of the abdomen (liver) and the plus direction (to the right of 0 on the axis of abscissas 0) represents the direction toward the lower part of the abdomen (anus).

Curve 4$a$ represents the distribution of total body adipose areas measured from medical images, curve 4$b$, that of hypodermic adipose, and curve 4$c$, abdominal adipose areas (each being the remaining area after the subtraction of the hypodermic adipose area from the total body adipose area in each position). Curves 4$a$, 4$b$ and 4$c$ are generated by plotting the areas acquired from medical images taken in different positions at the adipose distribution data computing step and interpolating the plotted points (to which the quadrangles correspond). In FIG. 4, abdominal adipose tissues around the rectum are defined to be adipose in contact with the rectum, and hypodermic adipose, adipose positioned outside the levator ani muscle.

On curves 4$a$, 4$b$ and 4$c$ of FIG. 4, the local maximum points of adipose areas (total body adipose area, hypodermic adipose area and abdominal adipose area) are not in the position of the navel (the axis of abscissas 0) but about 3 [cm] away from the navel toward the lower part of the abdomen. The hypodermic adipose area turns upward from a position about 10 [cm] below the navel, and much adipose is accumulated toward the buttocks together with the total body adipose area. However, the abdominal adipose area continuously decreases toward the anus in the pelvic cavity. Therefore, the adipose distribution curve 4$c$ of the abdominal adipose area in FIG. 4 has a local maximum point of abdominal adipose emerging about 3 [cm] away from the navel toward the lower part of the abdomen. At the abnormal shadow candidate detecting step, an abnormal shadow candidate is detected by detecting a local maximum point contained in the adipose distribution curve of the abdominal adipose area. Especially where the local maximum point is positioned about 3 [cm] below the navel as in FIG. 4, a suspicion of descending colon cancer is outputted as the result of detection.

(Step S102)

At this step, it is determined whether or not a random point on an adipose distribution curve is a local maximum point. If the point is determined to be a local maximum point (Yes), the processing advances to step S103 or, if it is not a local maximum point (No), to step S105.

Figure 6:
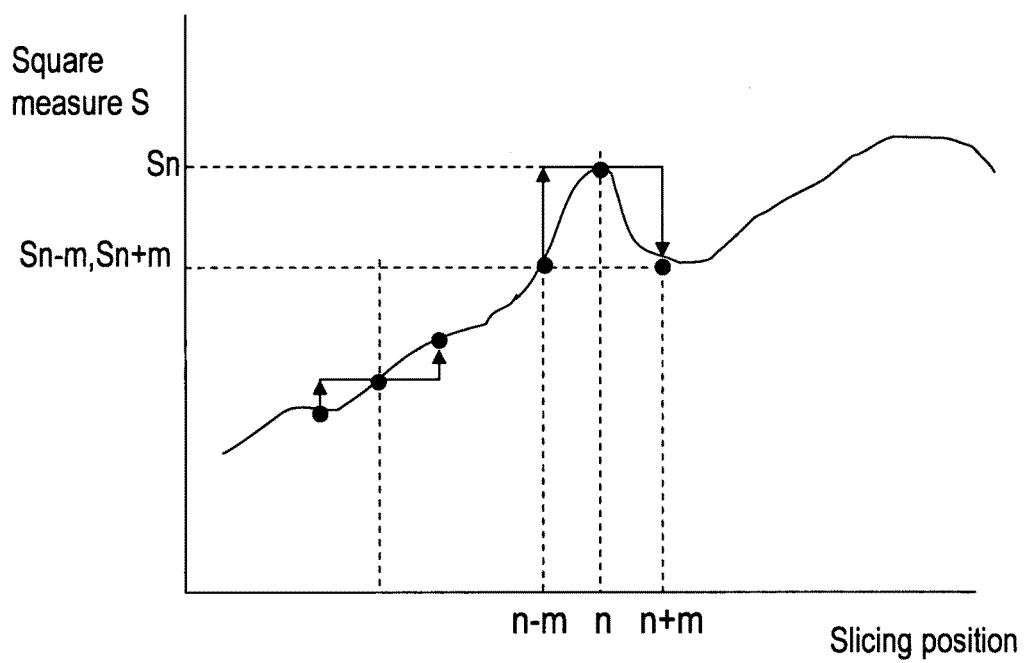
FIG. 6 shows processing to detect the local maximum point of the adipose distribution curve.

FIG. 5 and FIG. 6 illustrate processing to detect the local maximum point of the adipose distribution curve accomplished at the abnormal shadow candidate detecting step. FIG. 5 show an example of processing to detect a local maximum point. FIG. 5(A) shows the adipose area at each of points "a" through "h" on the adipose distribution curve. An emphasized value $\Delta S$ is figured out based on the square measure of the surroundings of each point. A formula to figure out the emphasized value $\Delta S$ is shown as Formula 1.

[Formula 1]

$$\Delta S = (Sc+Sd+Se+Sf)-(Sa+Sb+Sg+Sh) \quad (1)$$

FIG. 5(B) shows for each slicing position an emphasized value $\Delta S$ figured out by filtering. This graph makes the local maximum point easier to find by emphasizing the height of the local maximum point. At the abnormal shadow candidate detecting step, a point where the emphasized value $\Delta S$ is greater than a threshold $\alpha$ is detected as a local maximum point. This processing is a kind of filtering, and the local maximum point may as well be detected by using one or another of various other methods of filtering.

FIG. 6 shows another example of processing for local maximum point detection. At the abnormal shadow candidate detecting step, the image diagnosis support apparatus 20 may figure out adipose areas $Sn-m$, $Sn$ and $Sn+m$ with respect to a random point "n" and two points $n-m$ and $n+m$ ($m$ is a random number) before and after that, and determine the position of the point "n" which satisfies the condition of $Sn+m-Sn<0$ and $Sn-Sn-m>0$ as the position of the local maximum point.

(Step S103)

At the display step, the medical image corresponding to the local maximum point detected at S102 is displayed.

At the abnormal shadow candidate detecting step, the medical image corresponding to positional information in which the local maximum point detected at S102 is present (indicating the position of the local maximum point) is read out of the magnetic disk 12. At the display step, the read-out medical image is displayed. At the display step, the image diagnosis support apparatus 20 may as well display the portion corresponding to the positional information on the adipose distribution curve 61$a$, namely the designated pointer 61$b$ in a superposed manner. Further at the display step, a distribution curve indicating the adipose distribution data generated at the adipose distribution data computing step and its designated positional information are displayed superposed one over the other.

(Step S104)

At the display step, the display state at S103 is maintained, and placed in a sleep state for a prescribed length of time to make the displayed medical image or the adipose distribution curve more clearly visible.

(Step S105)

At S105, it is determined whether or not there is an instruction to stop displaying and, if there is (Yes), the processing advances to step S106 or, if there is not (No), to step S107.

At this step, the operator can read in detail the medical image 62 corresponding to a prescribed local maximum point of the adipose distribution curve. If there is an instruction to stop displaying, the prescribed display state is maintained until the stop is canceled at the next step S106.

(Step S106)

At S106, it is determined whether or not there is an instruction to cancel the stop and, if there is (Yes), the processing advances to step S107 or, if there is not (No), the stopped state continues to be maintained.

(Step S107)

At S107, a point on the adipose distribution curve to be filtered next is designated.

(Step S108)

At S108, it is determined whether or not to end filtering. If it is in the position to end filtering (Yes), the whole processing is ended or, if it is not (No), the processing returns to step S102 to repeat the sequence of processing.

Although the display step in the flow chart of FIG. 3 was described with reference to a case in which medical images 62 were displayed interlocked with the detection of local maximum points in the adipose distribution curve, it is also possible to detect local maximum points in advance and successively display only those medical images 62 from which the local maximum points were detected. In this way, only those medical images 62 from which local maximum points have been detected can be efficiently read. Thus, at the abnormal shadow candidate detecting step, at least one local maximum point in adipose distribution data (the adipose distribution curve) may be detected in advance, and abnormal shadow candidates may be successively detected regarding the pre-detected local maximum point.

In this mode for implementation, it is made possible to measure adipose areas from medical images, display the adipose distribution curve of the subject, detect local maximum points of that adipose distribution curve and present to the doctor the suspected presence of any abnormal shadow candidate. Further by concentrated examination of suspicious parts with a CAD apparatus to detect abnormal shadow candidates, the number of abnormal shadow candidates detected as manifesting false positive reactions can be expected to be made smaller than in the case of extracting abnormal shadow candidates from all the CT images; the distinction between real and false abnormal shadow candidates can be made more accurate, and their detection rate can be enhanced to minimize the number of cases of false positive reaction.

In the mode for implementation described above, when the distribution curve of the abdominal adipose area has any local maximum point, the presence of an abnormal shadow candidate is detected and tomograms are caused to be displayed. If the distribution curve of the abdominal adipose areas of healthy subjects also has any local maximum point, the configuration may as well be such that positional information on that emerging local maximum point is stored in the magnetic disk 12 in advance and, if a local maximum point corresponding to that positional information is detected at the abnormal shadow candidate detecting step, detection of an abnormal shadow candidate is refrained from.

Although the adipose distribution graph 61 and the medical image 62 are displayed in parallel in this mode for implementation as shown in FIG. 2, a switch-over displaying arrangement may as well be provided for instance to display either one of them. Or when no medical image 62 is displayed but only the adipose distribution graph 61a is shown for comparative display as in anamnestic observation or the like, the image diagnosis support apparatus 20 may generate only the adipose distribution graph 61.

Further, the image diagnosis support apparatus 20 may as well actuate the abnormal shadow candidate extracting step based on the abdominal adipose distribution curve, automatically extract an abnormal shadow candidate from the medical image 62 to be displayed, and display that abnormal shadow candidate in a different mode from other regions.

<Second Mode for Implementation>

A second mode for implementing the invention is a mode in which an abnormal shadow candidate is detected and the name of the presumable cancer case are displayed based on the correlation value between the adipose distribution pattern (the shape of the adipose distribution curve) of the subject and the adipose distribution pattern of a prescribed cancer case or the adipose distribution pattern of healthy subjects.

At the abnormal shadow candidate detecting step in this mode for implementation, when the correlation value between the adipose distribution curve corresponding to a prescribed disease case stored in the magnetic disk 12 and the adipose distribution curve generated by the distribution data computing device is greater than a prescribed value, the presence of an abnormal shadow candidate is detected.

Then at the display step, if the correlation value between the adipose distribution data generated at the abnormal shadow candidate detecting step and the adipose distribution data corresponding to the prescribed disease case is greater than the prescribed value, the disease name candidate is displayed.

In this mode for implementation, the program installed in the image diagnosis support apparatus 20 has, in addition to the above-described steps in the first mode for implementation, a storing step at which adipose distribution data corresponding to a prescribed disease case and the adipose distribution data of healthy subjects are stored into the magnetic disk 12 and a normalizing step at which normalization is accomplished to compare the adipose distribution data of the subject and the adipose distribution data corresponding to the prescribed disease case. When adipose distribution data of healthy subjects are to be stored here, the magnetic disk 12 corresponds to healthy subject's adipose distribution data or, when adipose distribution data corresponding to prescribed disease cases, to prescribed disease cases' adipose distribution data.

At the normalizing step, the adipose distribution data generated at the adipose distribution data computing step according to the adipose distribution data corresponding to a prescribed disease case or stored adipose distribution data of healthy subjects are normalized. Then, at the abnormal shadow candidate detecting step, the correlation value between the normalized adipose distribution data or the normalized adipose distribution data of healthy subjects and the normalized adipose distribution data of the subject is detected.

Figure 7:
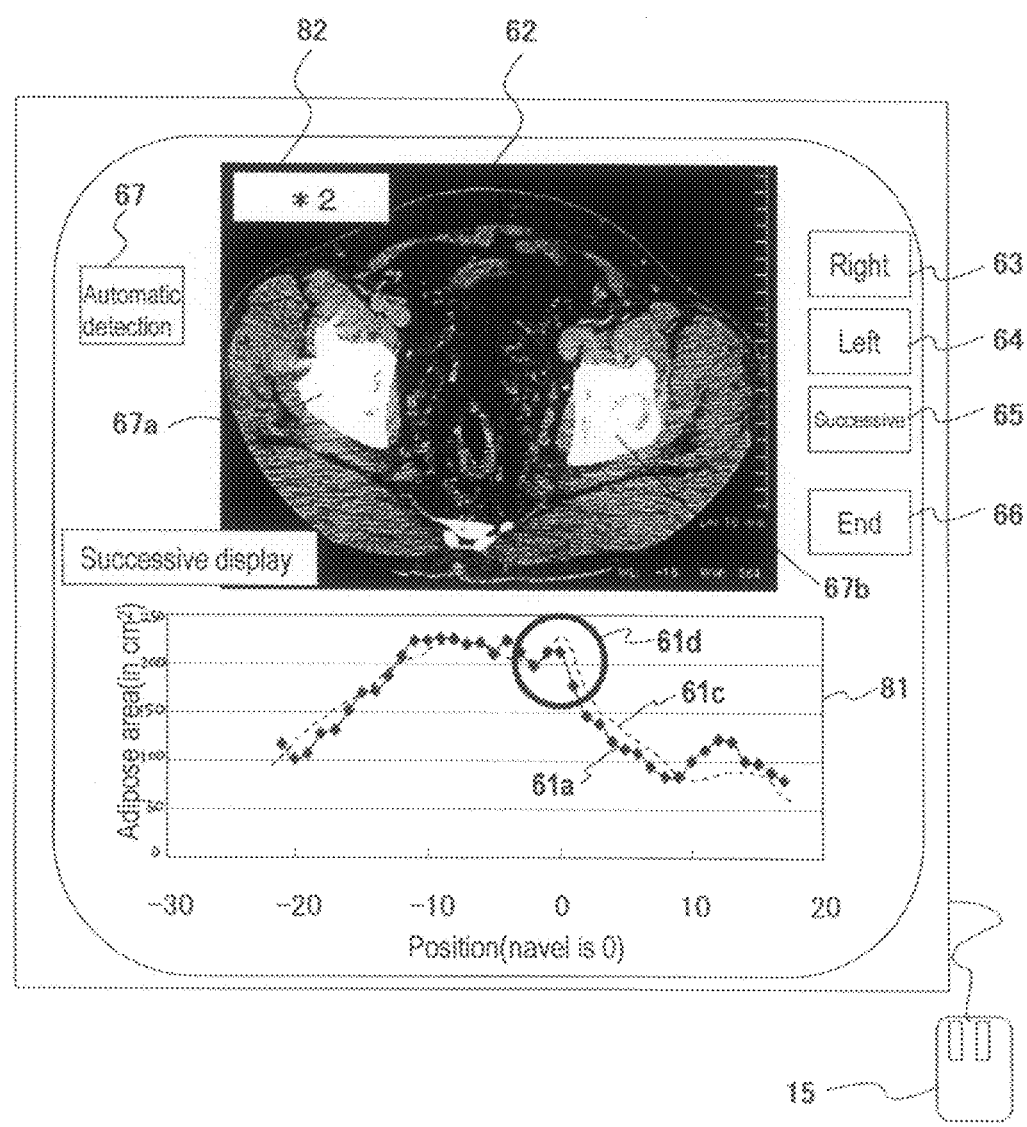
FIG. 7 shows a state in which the adipose distribution curve of a subject, a medical image and the names of diseases closely correlated to the adipose distribution curve of the subject are displayed.

FIG. 7 shows an example of screen displayed in this mode for implementation.

In FIG. 7, as in FIG. 2, an adipose distribution graph 81, the medical image 62, the right button 63, the left button 64, the successive button 65, the end button 66, the automatic detection button 67, a successive display button 69 and a message display area 82 are displayed. In the adipose distribution graph 81, the adipose distribution curve 61a of the subject and a disease case curve 61c for rectal cancer are displayed. A marker 61d is displayed superposed over the local maximum point of the adipose distribution curve 61a of the subject.

With reference to FIG. 7, the "automatic detection" button is operated to detect abnormal shadow candidates 67a and 67b. It is further indicated in the message display area 82 that the probability for those abnormal shadow candidates to be rectal cancer (first candidate) is about 80% and that of their being small intestinal cancer (second candidate) is about 10%.

As in the first mode for implementation, the operator designates a desired position on the adipose distribution curve 61a, and at the display step the medical image 62 corresponding to the designated position may be displayed.

Figure 8:
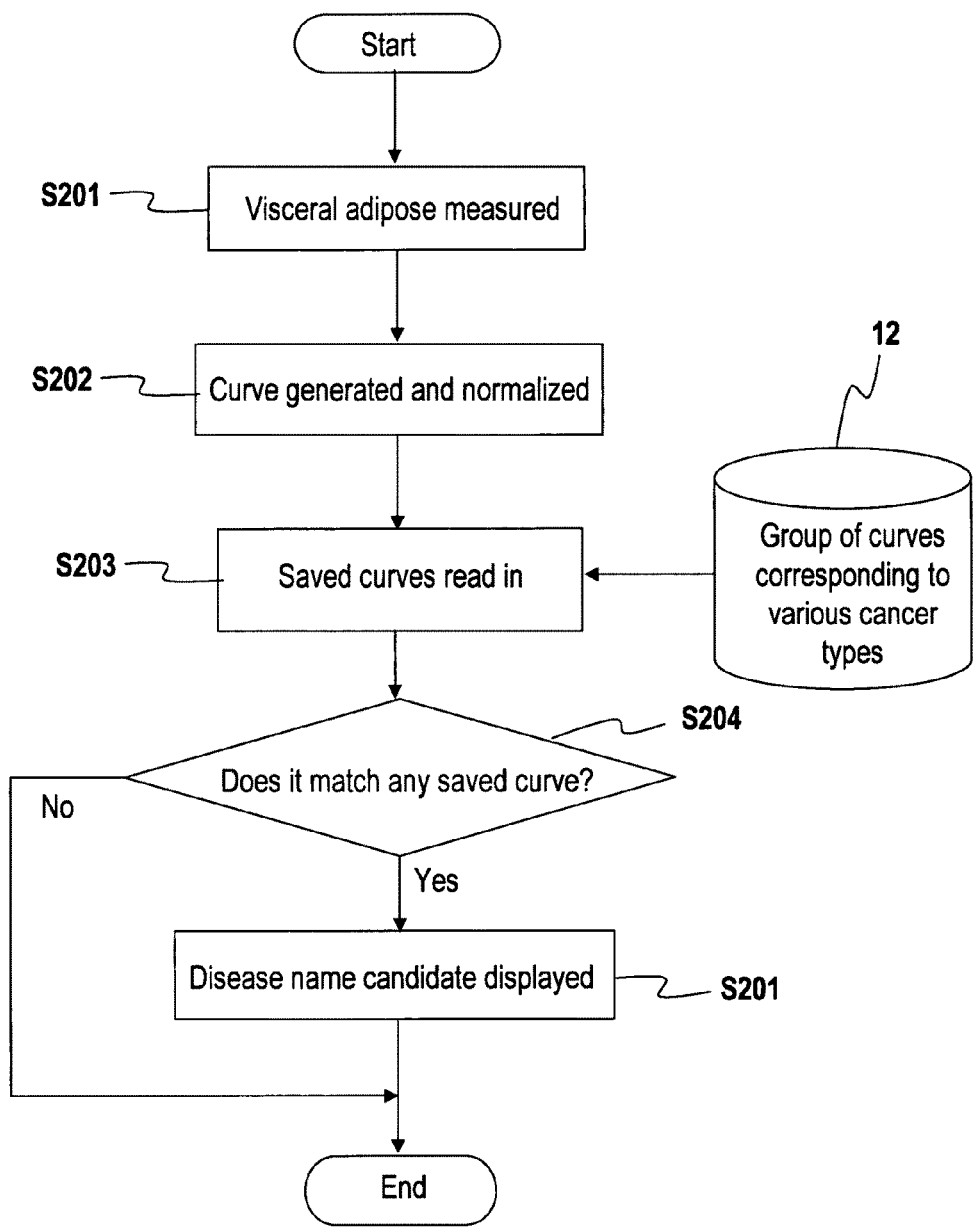
FIG. 8 is a flow chart of processing to output the names of diseases based on the correlation between the adipose distribution curve of the subject and the adipose distribution curve of each disease.

Next, processing in this mode for implementation will be described with reference to FIG. 8. FIG. 8 is a flow chart of processing by the image diagnosis support apparatus 20 to extract disease candidates based on the adipose distribution curve of the subject. The following description of the storing step will refer to a case of processing from a state in which normalized adipose distribution curves (sets of adipose distribution data each corresponding to a prescribed disease; hereinafter referred to as "disease case curve") corresponding to colon cancer, rectal cancer, gastric cancer or prostate cancer and conditions used for this normalization are stored in advance in the magnetic disk 12.

The following description will refer to a case of the adipose distribution data computing step where the adipose distribution curves are generated as in the description of the first mode for implementation.

(Step S201)

As at S101, the adipose area is measured from medical images of the subject at the adipose distribution data computing step to generate the adipose distribution curve.

(Step S202)

At the normalizing step, conditions for normalization are read out of the magnetic disk 12, and the adipose distribution curve of the subject generated at S201 is normalized. The purpose of this normalization is to normalize differences in physical constitution among a plurality of subjects to make comparison meaningful, because the height, width and other bodily aspects differ from subject to subject.

The normalization processing at the normalizing step is intended for comparison of the adipose distribution curve of the subject and the disease case curve by normalizing them under the same conditions; for instance, where the body height of the disease case curve differs from that of the subject, the adipose distribution curve of the subject may be multiplied by (the subject body height)/(the normalized body height). In this way, the disease case curve and the adipose distribution curve of the subject can be aligned with the navel position as 0. The conditions for normalization may be what permit considerations for individual differences in sex, weight and so forth besides the body height, which have to be taken into account in comparing the adipose distribution curve with the normalized disease case curve. At the display step, the normalized adipose distribution curve of the subject is displayed.

(Step S203)

At the abnormal shadow candidate detecting step, the disease case curves for various cancer cases (e.g. the adipose distribution curve 61c corresponding to rectal cancer) stored in a recording medium are read out of the magnetic disk 12. The read-out disease case curve and the subject's adipose curve normalized at step S202 may be comparably displayed.

The disease case curve stored in the magnetic disk 12 will be described in detail with reference to FIG. 9 through FIG. 12.

Figure 9:
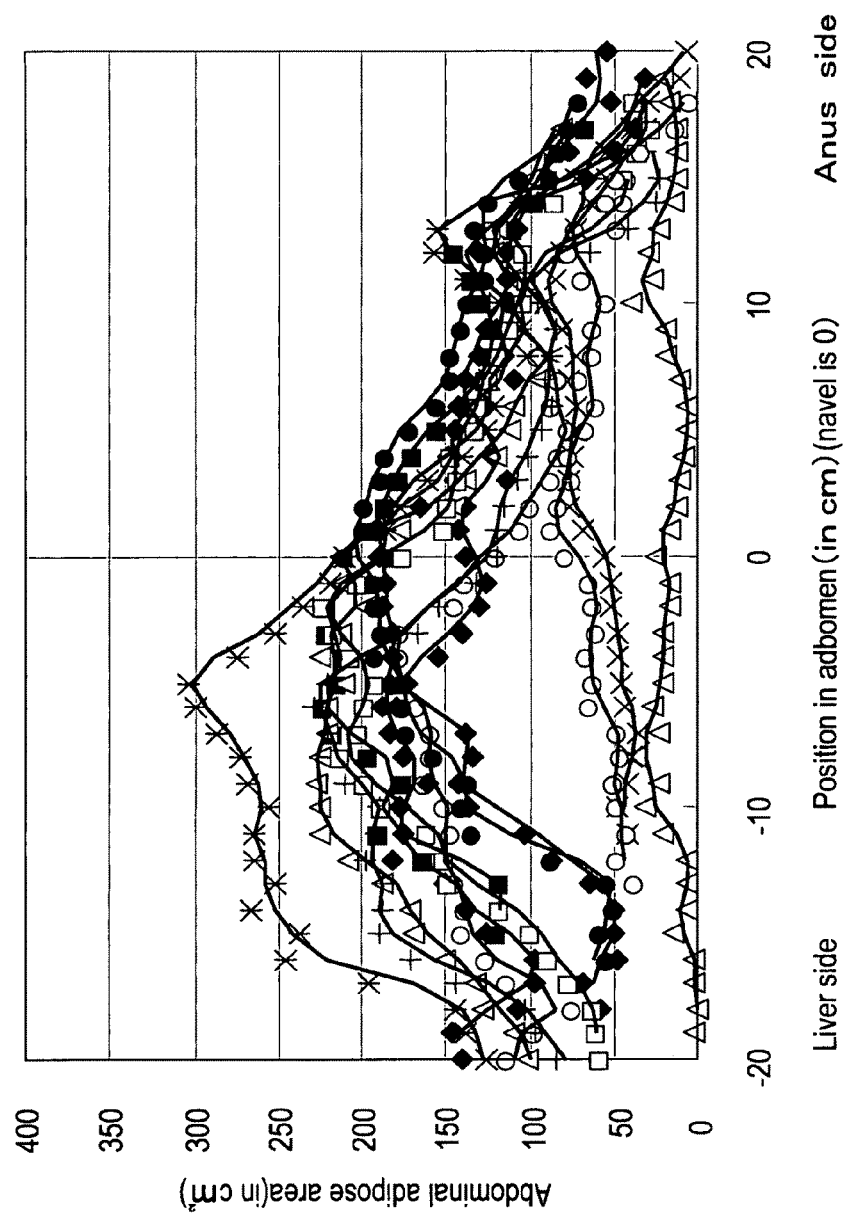
FIG. 9 shows the abdominal adipose distribution curves of cases of rectal cancer.

FIG. 9 shows the adipose distribution curves of many cases of rectal cancer. FIG. 9 covers many cases of obesity, measuring about 100 square centimeters or more in the navel position, and in many of these cases rectal cancer, a local maximum point is present at about 10 cm distances from the navel.

Figure 10:
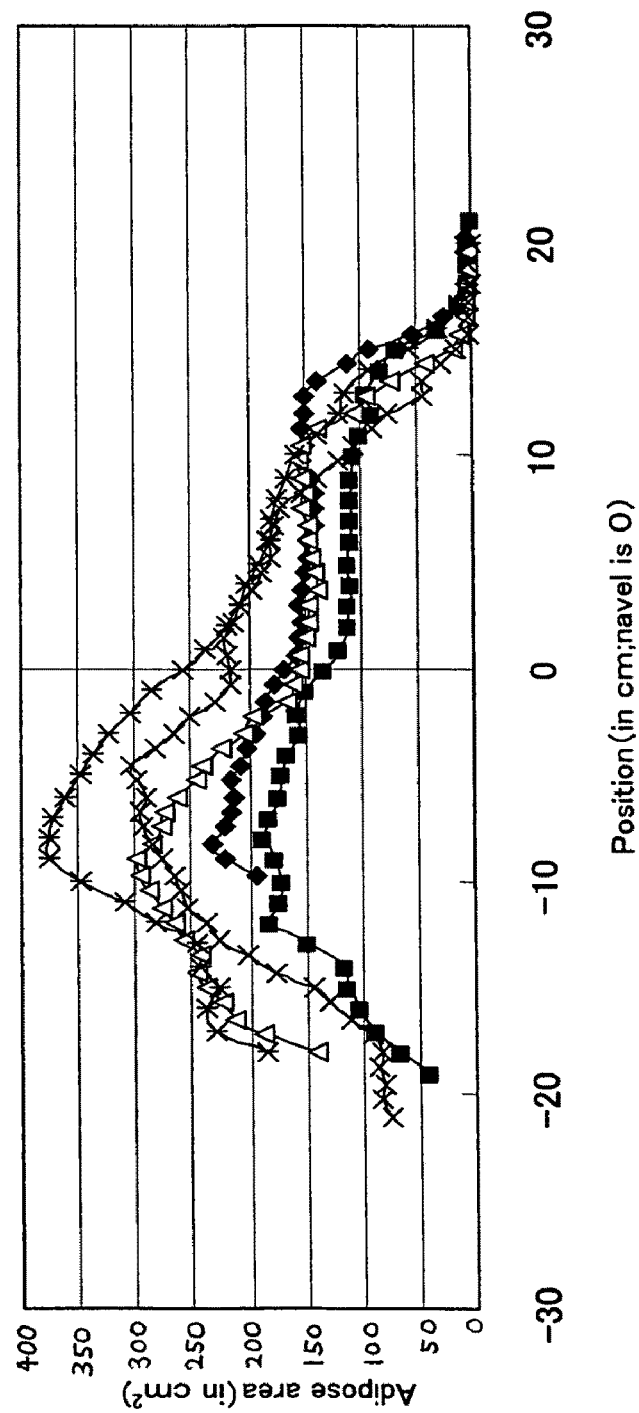
FIG. 10 shows the abdominal adipose distribution curves of cases of prostatic cancer.

FIG. 10 shows the adipose distribution curves of many cases of gastric cancer. As is evident from FIG. 12, though a local maximum point is found in some cases of gastric cancer, in 80% or more of cases, no plurality of local maximum points are observed on any adipose distribution curve.

Figure 11:
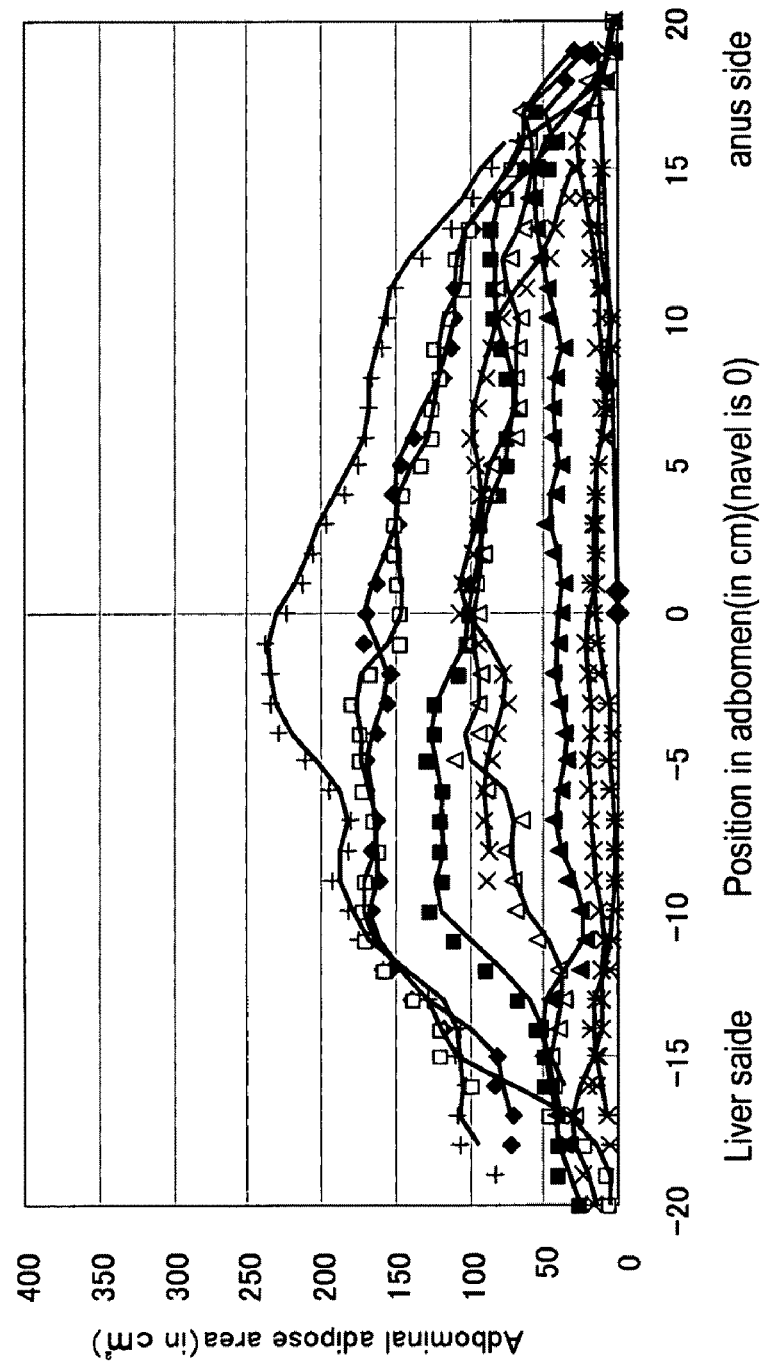
FIG. 11 shows the abdominal adipose distribution curves of cases of gastric cancer.

FIG. 11 shows the adipose distribution curves of many cases of prostate cancer. A plurality of local maximum point are found on each of the adipose distribution curves of prostate cancer cases, but the shape of the adipose distribution curves of prostate cancer cases is different from those of the adipose distribution curves of rectal cancer cases. Therefore, this type of cancer can be distinguished from rectal cancer.

The adipose distribution curves of these many cases undergo normalization processing to create a disease case curve representing each category of cases, resulting in the generation of normalized disease case curves. The normalized disease case curves are saved in the magnetic disk 12. One way of normalization processing is to average a large number of adipose distribution curves with respect to each prescribed case category of cancer.

(Step S204)

At the abnormal shadow candidate detecting step, each group of disease case curves corresponding to one or another of various cancer types read out at S203 is matched with the normalized adipose distribution curve of the subject to determine whether the two curves well match each other.

In more detail, at the abnormal shadow candidate detecting step, any correlation between the adipose distribution curve of the subject and the disease case curve is figured out by a pattern matching method or otherwise.

Figure 12:
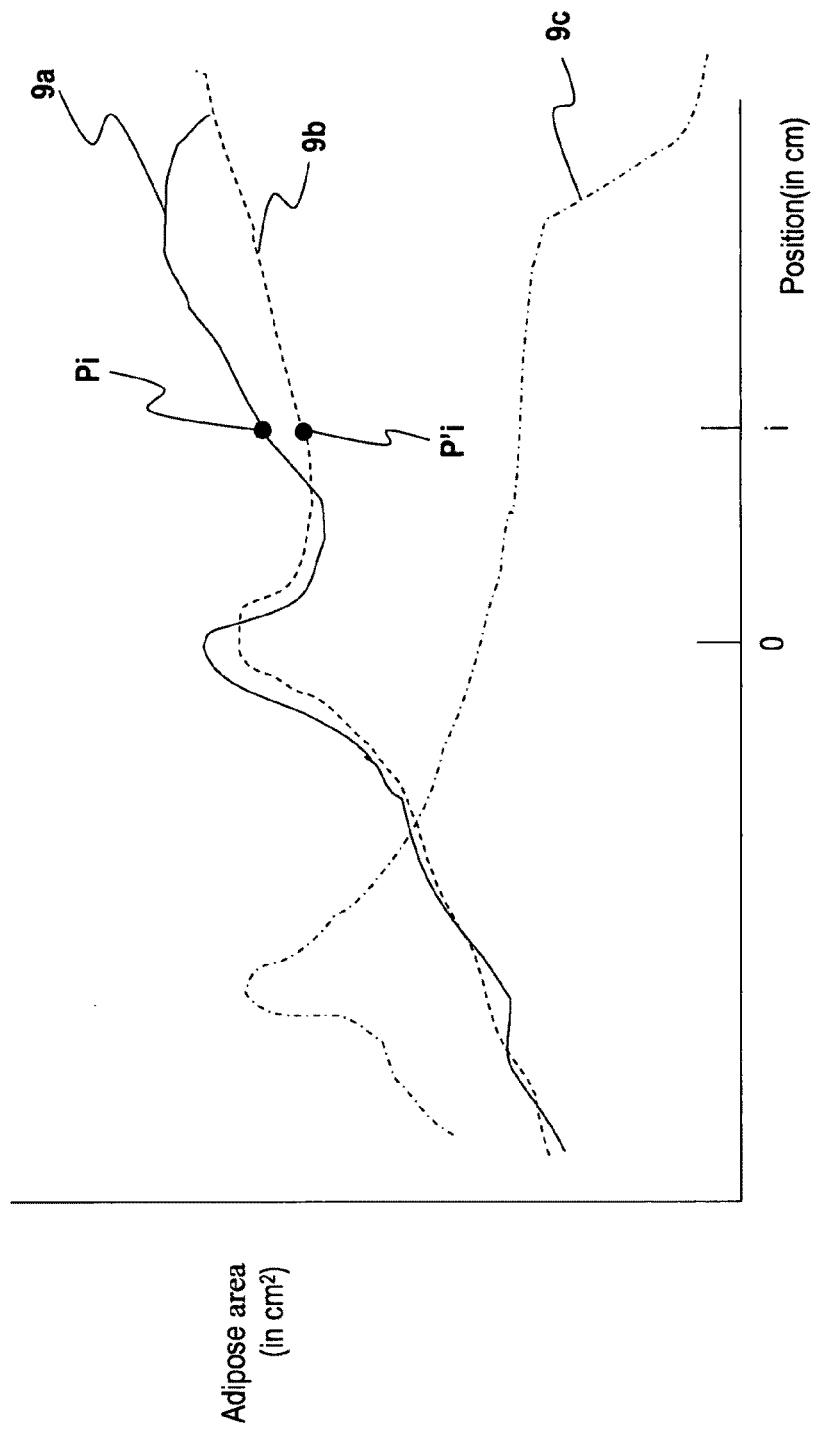
FIG. 12 shows pattern matching between the normalized adipose distribution curve of a subject and the adipose distribution curve of each disease.

A specific example of pattern matching at the abnormal shadow candidate detecting step will be described with reference to FIG. 12. FIG. 12 shows pattern matching between the normalized adipose distribution curve of the subject and disease case curves. In FIG. 12, a normalized adipose distribution curve 9a of the subject is expressed in a solid line, and disease case curves 9b and 9c are expressed in a dotted line and a one-point chain line, respectively.

The value of the adipose distribution curve of the subject and that of the disease case curve at each point on the adipose distribution curve (e.g. a point corresponding to a position of +i cm from the navel) being represented by Pi and P'i, respectively, pattern matching is processed in accordance with Formula 2. If the following condition is satisfied, the two curves are deemed to match each other.

[Formula 2]

$$\Sigma(Pi-P'i)^2 < \text{Certain value} \tag{2}$$

When the patterns of the adipose distribution curve of the subject and the disease case curve match each other (Yes), the processing advances to S205, or when those of the adipose distribution curve of the subject and the disease case curve do not match each other (No), the processing is ended. At the abnormal shadow candidate detecting step, if the variance between the adipose distribution curve of the subject and the disease case curve is smaller than the certain value, the patterns of the adipose distribution curve of the subject and the disease case curve are determined to match each other, and the presence of an abnormal shadow candidate is detected. Further at the abnormal shadow candidate detecting step, the name of the disease is outputted as the result of detection.

Although the foregoing description referred to a case in which pattern matching was processed at the abnormal shadow candidate detecting step by using a variance, it is also possible to detect any correlation between the adipose distribution curve of the subject and the disease case curve and to determine that their patterns should be matched if a correlation value of or above a prescribed level is found. In this case, at the abnormal shadow candidate detecting step, the probability for the subject to fit the outputted cancer case may be figured out based on the extent of correlation between the adipose distribution curve of the subject and the disease case curve. As the correlation value, for instance one corresponding to the level of variance or standard deviation may be figured out, or a correlation value of 0 to 1 may be figured out from the inclination of the two curves by using the method of least squares. When a correlation value of 0 to 1 has been figured out, the probability may be calculated by multiplying this value by 100.
(Step S205)

At the display step, the disease name corresponding to the disease case curve matching the adipose distribution curve of the subject is displayed in the message display area 82 to end processing.

The program executed by the CPU 10 further has a disease case fitting probability computing step at which the probability for the subject to fit any disease case based on the correlation value detected at the abnormal shadow candidate detecting step; at the display step, if there are a plurality of disease case curves matching the pattern of the adipose distribution curve of the subject, priority order, such as the first candidate and the second candidate, may be assigned according to the relative level of correlation between the adipose distribution curve of the subject and the disease case curve, and disease name candidates together with their probabilities may be displayed according to the order of priority. Alternatively, at the display step, only the adipose distribution graph 81 may be displayed, or only the disease name corresponding to the disease case curve matching the adipose distribution curve of the subject may be displayed. In the message display area 82, the disease name of the candidate which may fit the subject and the probability of fitting that disease are displayed.

Incidentally at the abnormal shadow candidate detecting step, it is also possible to predict based on the correlation value computed at S204 whether or not the subject is diathetically susceptible to cancer and to display at the display step a message indicating the prediction. It is also possible to predict based on the value of correlation with the disease case curve the probability for the subject to contract a malignant tumor or the like at the adipose distribution data computing step instead of the abnormal shadow candidate detecting step and to display the predicted probability of contraction at the display step.

In this way, the subject can be numerically informed of his or her own susceptibility to cancer, and the doctor can be provided with an indicator according to which guidance on lifestyle improvement is given to prevent the patient from contracting the disease.

Incidentally, the program executed by the CPU 10 may further have a display control step at which a successive display button 68 for successively displaying on the CRT 14 screen in a prescribed sequence the sets of adipose distribution data generated at the adipose distribution data computing step. The operator may input with the mouse 15 to the successive display button 68 whose displaying is so controlled.

In this way, at the display control step, sets of adipose distribution data displayed on the CRT 14 are successively displayed according to the successive displaying function of the successive display button 68 inputted with the mouse 15. For instance, adipose distribution data on the stomach, liver, the upper part of the abdomen, the lower part of the abdomen and the intestines are successively displayed.

In the mode for implementation described above, the presence or absence of suspected cancer can be detected based on any correlation between the adipose distribution curve of the subject and adipose distribution curves corresponding to cancer cases. Further in this mode for implementation, the suspected disease name and the probability for contraction of that disease are displayed, and a medical image picked up in the position of the subject where the contraction of that cancer is suspected can be displayed.

Although the presence of cancer is detected based on the correlation value between the disease case curve corresponding to a disease case and the adipose distribution curve of the subject in the mode for implementation described above, the presence of cancer can as well be detected based on the correlation value between the adipose distribution curves of healthy subjects and the adipose distribution curve of the subject. In this case, normalized adipose distribution curves of healthy subjects are stored in advance in the magnetic disk 12. At the abnormal shadow candidate detecting step, if the correlation value between the adipose distribution curve curves of healthy subjects stored in the magnetic disk 12 and the adipose distribution curve of the subject is smaller than a prescribed level, the presence of an abnormal shadow candidate is detected.

More specifically, first the above-described steps S201 and S202 are executed, and at S203 the adipose distribution curves of healthy subjects are read out of the magnetic disk 12 at the abnormal shadow candidate detecting step.

Then at S204, the value of correlation with the adipose distribution curves of healthy subjects is figured out at the abnormal shadow candidate detecting step and, if the correlation value is not smaller than the prescribed level, it is determined that there is no abnormal shadow candidate and the processing advances to NO. If the correlation value is smaller than the prescribed level, this is determined to mean YES and the processing advances to S205.

At S205, the presence of an abnormal shadow candidate is displayed instead of a disease name. This enables an abnormal shadow candidate to be detected by using the value of correlation with the adipose distribution curves of healthy subjects.

At the abnormal shadow candidate detecting step, pattern matching between the adipose distribution curve of the subject and the adipose distribution curves of healthy subjects is accomplished to detect any position where the correlation value is smaller than the prescribed level; at the display step, only the medical image 62 corresponding to the detected position may be displayed.

<Third Mode for Implementation>

This mode for implementation is a mode in which the adipose distribution curve of the subject is displayed, and the operator determines the presence or absence of any abnormal shadow candidate based on the adipose distribution curve. Further to support the operator in his or her determination, the image diagnosis support apparatus 20 may comparably display the adipose distribution curve of the subject and the adipose distribution curves of healthy subjects and/or disease case curves.

Figure 13:
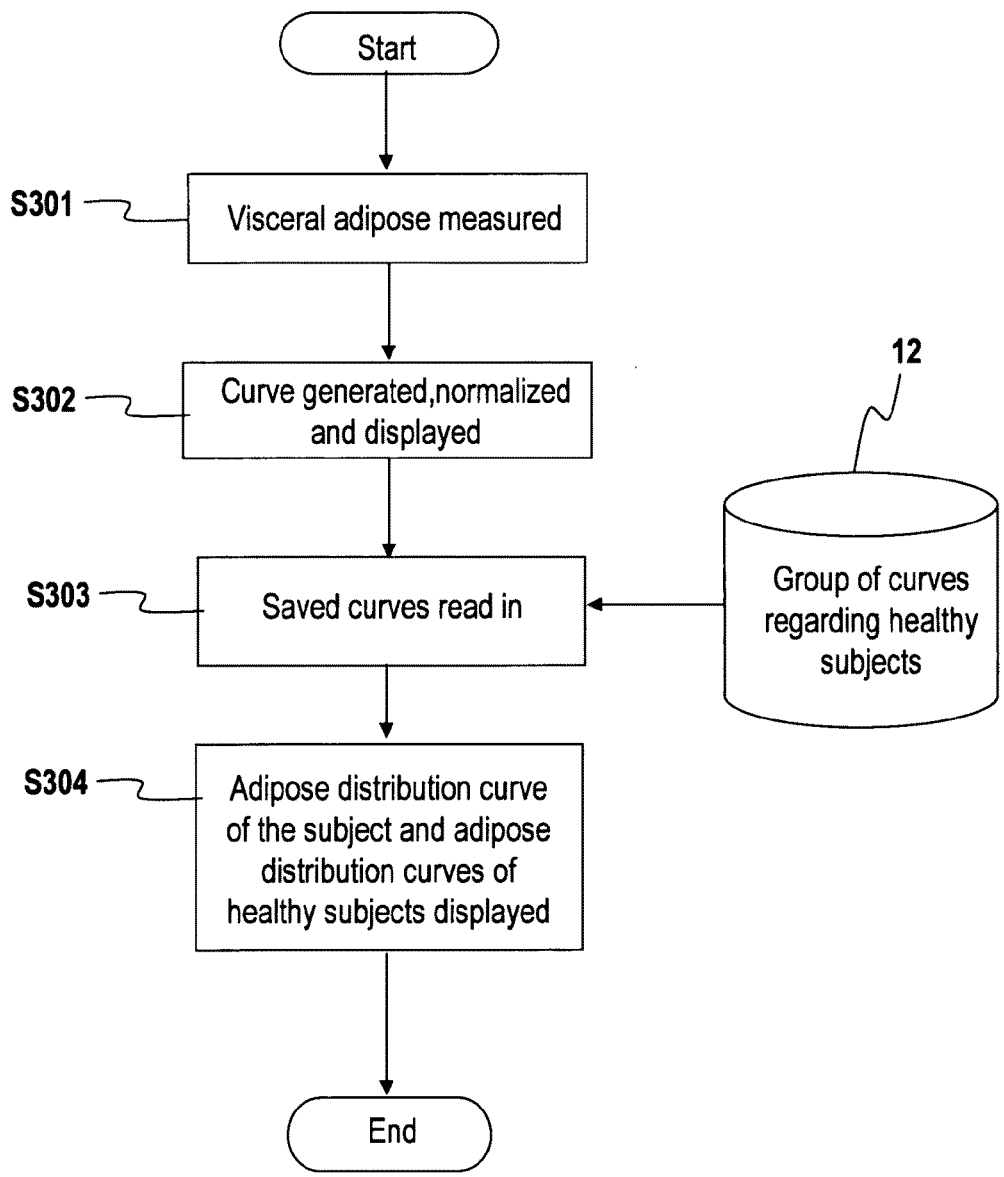
FIG. 13 is a flow chart of processing to comparably display the adipose distribution curve of a subject and the adipose distribution curves of healthy subjects.

Processing in this mode for implementation will be described with reference to FIG. 13. FIG. 13 is a flow chart of processing to comparably display the adipose distribution curve of the subject and the adipose distribution curves of healthy subjects. The adipose distribution curves of healthy subjects are stored in advance in the magnetic disk 12, and the following processing is started in this state.
(Steps S301 through S302)

As in S201 through S202, the adipose distribution curve of the subject is generated and normalized at the adipose distribution data computing step. And the adipose distribution curve of the subject is displayed at the display step. This enables the operator to visually recognize the adipose distribution curve of the subject.

(Step S303)

At the display step, the normalized adipose distribution curves of healthy subjects (hereinafter referred to as "healthy curves") are read in from the magnetic disk 12.

(Step S304)

At the display step, the adipose distribution curve of the subject and the healthy subjects are comparably displayed. For instance at the display step, the adipose distribution curve of the subject and the healthy curves are displayed on the adipose distribution graph one superposed over the other.

Although the image diagnosis support apparatus 20 comparably displays the healthy curves in the mode for implementation described above, a disease case curve may as well be comparably displayed. In that case, the image diagnosis support apparatus 20 may as well select and display a disease case curve the operator desires out of a plurality of kinds of disease case curves by, for instance, a pull-down menu.

Also, the image diagnosis support apparatus 20 may be provided with designating device for designating any desired position on the adipose distribution curve of the subject displayed at the display step, such as the aforementioned pointer 61b for example, and display a medical image corresponding to a region in the adipose distribution curve of the subject indicated by the operator with the pointer 61b.

The image diagnosis support apparatus 20 may be further provided with local maximum point detecting device, detect a local maximum point from the adipose distribution curve of the subject displayed at S302 and display a marker superposed over the local maximum point.

<Other Modes for Implementation>

While the adipose distribution curve and medical images of the subject are displayed at the display step in the modes for implementation described above, a message indicating the presence or absence of any abnormal shadow candidate or a message indicating positional information on the presence of an abnormal shadow candidate may be displayed as well. More specifically, positional information on the presence of an abnormal shadow candidate in the subject is detected at the abnormal shadow candidate detecting step. And at the display step, a message indicating the detected positional information is displayed.

Figure 14:
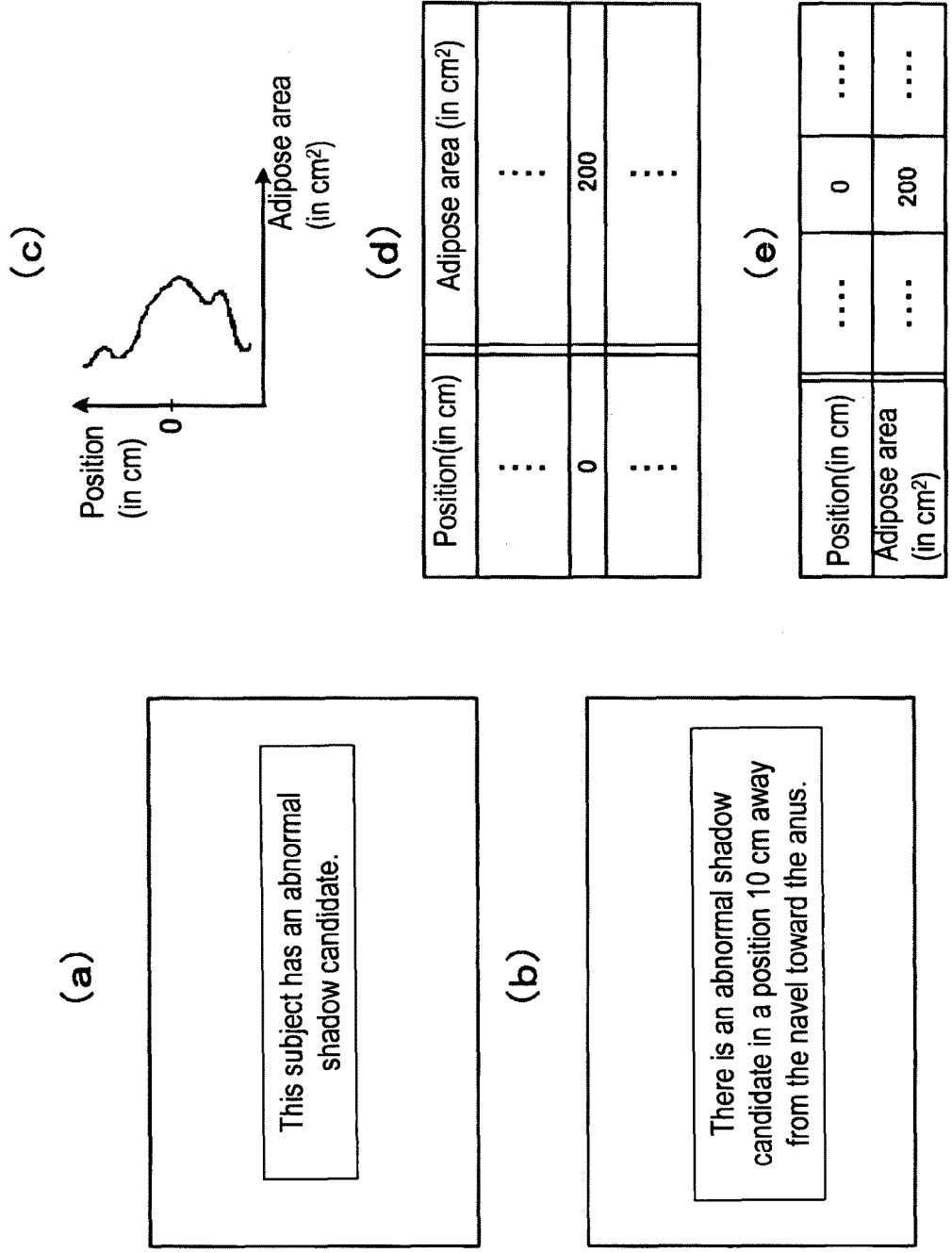
FIG. 14(a) shows an example of displayed message indicating the presence or absence of any abnormal shadow candidate.
FIG. 14(b), an example of displayed message indicating the position of an abnormal shadow candidate.
FIG. 14(c), an example of adipose distribution curve.
FIG. 14(d), an example of adipose distribution table.
FIG. 14(e), another example of adipose distribution table.

FIG. 14(a) shows an example of displayed message indicating the presence or absence of any abnormal shadow candidate. The image diagnosis support apparatus 20 may as well display a message indicating the result of automatic detection of an abnormal shadow candidate, for instance detection of an abnormal shadow candidate based on the local maximum point or of detection of an abnormal shadow candidate based on the value of correlation with the adipose curve of healthy subjects or the value of correlation with the disease case curves, such as "Subject has an abnormal shadow candidate".

FIG. 14(b) shows an example of displayed message indicating the position of an abnormal shadow candidate. In FIG. 14(b), in addition to the presence or absence of an abnormal shadow candidate, a message indicating positional information on the presence of an abnormal shadow candidate, such as "There is an abnormal shadow candidate in a position 10 cm away from the navel toward the anus", is displayed.

Also, while the axis of abscissas of the adipose distribution graph represents the position in the subject and the axis of ordinates represents the adipose area in that position at the adipose distribution data computing step in the mode for implementation described above, an adipose distribution graph in which the axis of ordinates represents the position in the subject and the axis of abscissas represents the adipose area as shown in FIG. 14(c) may be generated as well.

Further, while the adipose distribution graph is generated at the adipose distribution data computing step in the mode for implementation described above, what can be generated here is not limited to this, but an adipose distribution table (indicating adipose area information) in which the rows and columns respectively represent positions in the subject and adipose areas acquired from the medical images picked up in the respective positions may also be generated. At the display step, the generated adipose 1 5 distribution table may be displayed.

FIG. 14(d) shows an example of adipose distribution table. In FIG. 14(d), the left column lists positions in the subject and the right column, adipose areas in the respective positions. FIG. 14(e) shows another example of adipose distribution table.

In FIG. 14(e), the upper row lists positions in the subject and the lower row, in the respective positions.

Figure 15:
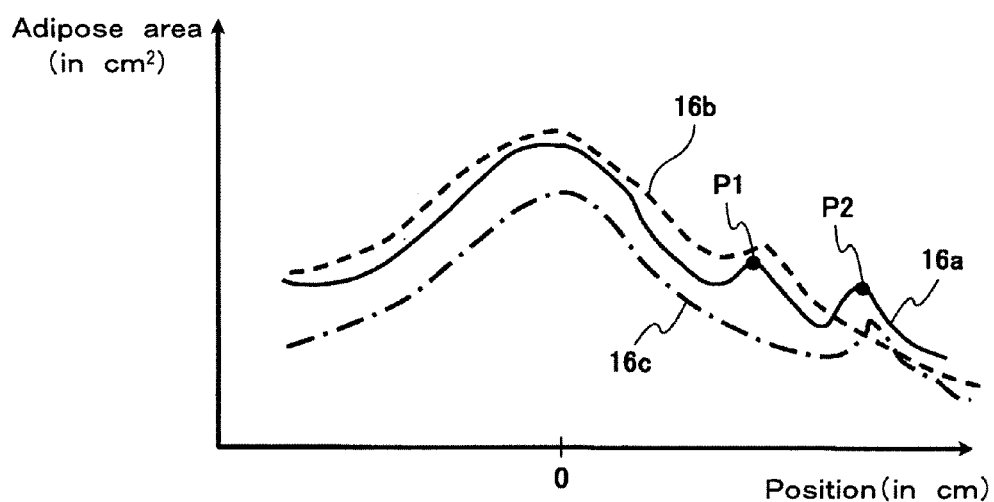
FIG. 15 shows local maximum points respectively fitting a plurality of diseases.

Further at the abnormal shadow candidate detecting step, local maximum points each corresponding to one or another of a plurality of disease cases may be detected on the adipose distribution curve of the subject. FIG. 15 shows local maximum points respectively fitting a plurality of diseases. In FIG. 15, an adipose distribution curve 16a of the subject is expressed in a solid line, a disease case curve 16b in a dotted line, and a disease case curve 16c corresponding to colon cancer in a one-point chain line.

At the abnormal shadow candidate detecting step, p1 may be detected as a local maximum point corresponding to rectal cancer, and p2, as a local maximum point corresponding to colon cancer.

Also, the program executed by the CPU 10 of the image diagnosis support apparatus 20 may further have the display control step of causing at least one scroll button for scrolling the adipose distribution data, generated at the adipose distribution data computing step, in a prescribed direction on the screen of the CRT 14 to be displayed and input device (such as the mouse 15) for the operator to input to that at least one scroll button under display control. In this case, at the display control step, adipose distribution data displayed on the CRT 14 are scroll-displayed according to the scrolling function of the scroll button inputted with the mouse 15.

Figure 16:
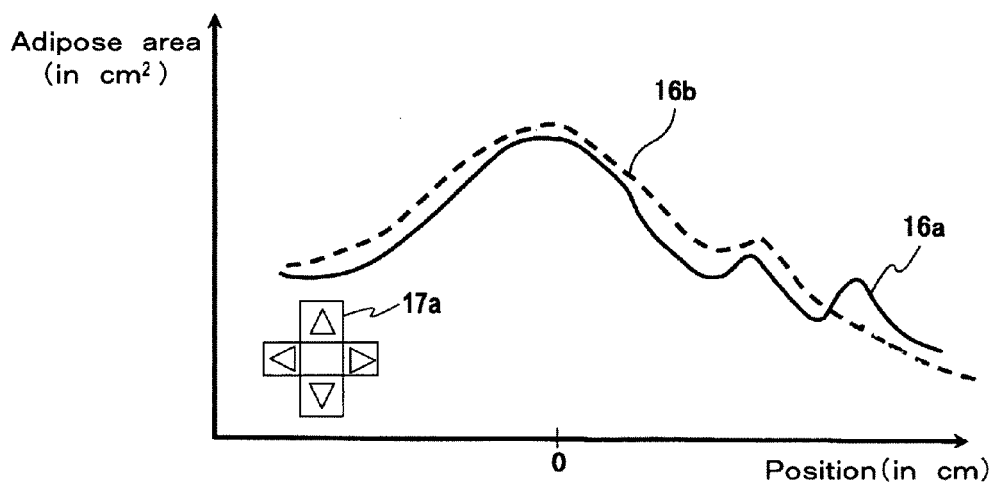
FIG. 16 shows an example of screen display containing scroll buttons.

FIG. 16 shows an example of screen display containing scroll buttons 17a. Referring to FIG. 16, the operator can move the adipose distribution curve 16a or the disease case curve 16b of the subject on the screen back and forth and/or right and left by manipulating the scroll buttons 17a with the mouse 15. This enables the operator to compare a plurality of adipose distribution curves irrespective of whether or not the adipose distribution curve 16a of the subject is normalized.

INDUSTRIAL APPLICABILITY

The invention can be used not only with respect to cancer cases but also for the purpose of presenting, based on adipose distribution data on the subject, the suspected presence of other cases correlated to the presence of adipose tissues.

The invention claimed is:

1. An image diagnosis support apparatus comprising:
an adipose distribution data computing device which figures out adipose distribution data and a local maximum point of the figured-out adipose distribution data, measured of a desired site in a subject from at least one medical image;

an abnormal shadow candidate detecting device which detects an abnormal shadow candidate based on the local maximum point of the figured-out adipose distribution data; and a display device which displays the abnormal shadow candidate detected by the abnormal shadow candidate detecting device and the medical image in a manner of being related to each other.

2. The image diagnosis support apparatus according to claim 1, wherein:

the abnormal shadow candidate detecting device detects positional information on a presence of the abnormal shadow candidate in the subject; and the display device displays a message indicating the detected positional information.

3. The image diagnosis support apparatus according to claim 2, further comprising:

an abnormal shadow candidate extracting device which extracts the abnormal shadow candidate detected by the abnormal shadow candidate detecting device from the medical image;

wherein:

the display device displays the abnormal shadow candidate extracted by the abnormal shadow candidate extracting device and the medical image in a manner of being related to each other.

4. The image diagnosis support apparatus according to claim 1, wherein:

the adipose distribution data computing device generates an adipose distribution curve in which one axis represents positions in the subject and the other axis represents a distribution of adipose areas acquired from medical images taken in the positions; and the display device displays the adipose distribution curve.

5. The image diagnosis support apparatus according to claim 1, wherein:

the adipose distribution data computing device generates an adipose distribution table in which rows and columns respectively represent positions in the subject and adipose areas acquired from medical images taken in the positions, and the display device displays the adipose distribution table.

6. The image diagnosis support apparatus according to claim 1, wherein:

the abnormal shadow candidate detecting device detects at least one local maximum point in the adipose distribution data, and detects the abnormal shadow candidate based on the detected local maximum point.

7. The image diagnosis support apparatus according to claim 1, further comprising:

a healthy subject adipose distribution data storing device which stores adipose distribution data of healthy subjects, wherein:

the abnormal shadow candidate detecting device detects a presence of an abnormal shadow candidate when a correlation value between the adipose distribution data of healthy subjects stored in the healthy subject adipose distribution data storing device and the adipose distribution data generated by the adipose distribution data computing device is below a prescribed level.

8. The image diagnosis support apparatus according to claim 1, further comprising:

a prescribed disease adipose distribution a data storing device which stores adipose distribution data corresponding to prescribed disease cases, wherein:

the abnormal shadow candidate detecting device detects a presence of an abnormal shadow candidate when a correlation value between the adipose distribution data corresponding to a prescribed disease case stored in the prescribed disease case stored in the prescribed disease adipose distribution data storing device and the adipose distribution data generated by the adipose distribution data computing device is above a prescribed level.

9. The image diagnosis support apparatus according to claim 8, wherein:

the display device, when a correlation value between the adipose distribution data generated by the abnormal shadow candidate detecting device and the adipose distribution data corresponding to a prescribed disease case is above a prescribed level, displays a disease name candidate.

10. The image diagnosis support apparatus according to claim 1, further comprising:

a healthy subject adipose distribution data storing device which stores adipose distribution data of healthy subjects;

a prescribed disease adipose distribution data storing device which stores adipose distribution data corresponding to prescribed disease cases; and a normalizing device which normalizes the stored adipose distribution data corresponding to prescribed disease cases or the stored adipose distribution data of healthy subjects and the adipose distribution data generated by the adipose distribution data computing device, wherein:

the abnormal shadow candidate detecting device detects a correlation value between the normalized adipose distribution data corresponding to a prescribed disease case or the normalized adipose distribution data of healthy subjects and the normalized adipose distribution data of the subject.

11. The image diagnosis support apparatus according to claim 10, further comprising:

a case fitting probability computing device which computes a probability for the subject to fit the disease case based on the correlation value detected by the abnormal shadow candidate detecting device, wherein:

the display device displays he computed probability.

12. The image diagnosis support apparatus according to claim 1, further comprising:

a display control device which causes at least one scroll button for scrolling the adipose distribution data generated by the adipose distribution data computing device in a prescribed direction of a screen of the display device to be displayed; and an input device via which an operator inputs to the at least one scroll button under display control, wherein:

the display control device scroll-displays, according to a scrolling function of the scroll button inputted via the input device, the adipose distribution data displayed on the display device.

13. The image diagnosis support apparatus according to claim 1, further comprising:

a display control device which causes a successive display button for successively displaying the adipose distribution data generated by the adipose distribution data computing device in a prescribed order on a screen of the display device to be displayed; and an input device via which an operator inputs to the successive display button under display control, wherein:

the display control device successively displays, according to a successive display function of the successive display button inputted via the input device, the adipose distribution data displayed on the display device.

14. The image diagnosis support apparatus according to claim 1, wherein:
the display device displays the abnormal shadow candidate detected by the abnormal shadow candidate detecting device in a display mode differentiated from areas other than the abnormal shadow candidate in the medical image.

15. The image diagnosis support apparatus according to claim 14, wherein:
the display device displays the abnormal shadow candidate and areas differing from the abnormal shadow candidate by using a different display color, superposing a marker, flashing the abnormal shadow candidate area or combining some of these display modes.

16. The image diagnosis support apparatus according to claim 1, wherein:
the display device displays, superposed one over the other, a distribution curve indicating adipose distribution data generated by the adipose distribution data computing device and positional information designated thereon.

17. The image diagnosis support apparatus according to claim 1, wherein:
the display device, in a presence of a plurality of disease case curves matching the pattern of a distribution curve indicating the adipose distribution data generated by the adipose distribution data computing device, assigns precedence in the descending order of a correlation value between the adipose distribution curve of the subject and the disease case curve and displays the disease name candidates and the probabilities thereof in the order of assigned precedence.

18. The image diagnosis support apparatus according to claim 17, wherein:
the adipose distribution data computing device predicts a probability for the subject to contract a malignant tumor or the like based on the correlation value between the adipose distribution curve of the subject and the disease case curve; and
the display device displays the predicted probability of contraction.

19. An image diagnosis support apparatus comprising:
an adipose distribution data computing device which figures out adipose distribution data measured of a desired site in a subject from at least one medical image;
an abnormal shadow candidate detecting device which detects an abnormal shadow candidate based on the figured-out adipose distribution data; and
a display device which displays the abnormal shadow candidate detected by the abnormal shadow candidate detecting device and the medical image in a manner of being related to each other, wherein:
the abnormal shadow candidate detecting device detects in advance at least one local maximum point in the adipose distribution data and successively detects the abnormal shadow candidate for each of the pre-detected local maximum points.

20. A method performed by an image diagnosis support apparatus, the method comprising:
(a) determining, by an adipose distribution data computing part of the image diagnosis support apparatus, adipose distribution data and a local maximum point of the adipose distribution data, measured of a desired site in a subject from at least one medical image;
(b) detecting, by an abnormal shadow candidate detecting part of the image diagnosis support apparatus, an abnormal shadow candidate based on the local maximum point of the adipose distribution data determined in (a); and
(c) displaying the abnormal shadow candidate detected in (b) and the medical image manner of being related to each other.

* * * * *

UNITED STATES PATENT AND TRADEMARK OFFICE
CERTIFICATE OF CORRECTION

| | | |
|---|---|---|
| PATENT NO. | : 8,027,524 B2 | Page 1 of 1 |
| APPLICATION NO. | : 11/795486 | |
| DATED | : September 27, 2011 | |
| INVENTOR(S) | : Ogura et al. | |

It is certified that error appears in the above-identified patent and that said Letters Patent is hereby corrected as shown below:

Title Page

Replace the PCT Number section on the cover page of the patent, with the following:

Item --(86)   PCT No.:  PCT/JP2006/300644--

Signed and Sealed this
Twenty-second Day of November, 2011

David J. Kappos
*Director of the United States Patent and Trademark Office*